United States Patent
de Fátima Scarparo de Sanctis et al.

(10) Patent No.: US 11,013,671 B2
(45) Date of Patent: *May 25, 2021

(54) SYNERGISTIC HAIR CARE FORMULATIONS

(71) Applicants: Rohm and Haas Company, Collegeville, PA (US); Dow Brasil Sudeste Industrial Ltda., Sao Paulo/Sp (BR); Dow Global Technologies LLC, Midland, MI (US)

(72) Inventors: Daisy de Fátima Scarparo de Sanctis, Sao Paulo (BR); Nikhil J. Fernandes, Philadelphia, PA (US); David L. Malotky, Midland, MI (US); Jodi A. Thomas, Midland, MI (US)

(73) Assignees: Rohm and Haas Company, Philadelphia, PA (US); Dow Brasil Sudeste Industrial Ltda., Sao Paulo (BR); Dow Global Technologies LLC, Midland, MI (US)

( * ) Notice: Subject to any disclaimer, the term of this patent is extended or adjusted under 35 U.S.C. 154(b) by 337 days.

This patent is subject to a terminal disclaimer.

(21) Appl. No.: 16/305,504

(22) PCT Filed: Nov. 30, 2016

(86) PCT No.: PCT/US2016/064096
§ 371 (c)(1),
(2) Date: Nov. 29, 2018

(87) PCT Pub. No.: WO2017/218035
PCT Pub. Date: Dec. 21, 2017

(65) Prior Publication Data
US 2020/0323746 A1    Oct. 15, 2020

Related U.S. Application Data

(60) Provisional application No. 62/350,356, filed on Jun. 15, 2016.

(51) Int. Cl.
| | | |
|---|---|---|
| *A61K 8/06* | (2006.01) | |
| *A61K 8/31* | (2006.01) | |
| *A61K 8/41* | (2006.01) | |
| *A61K 8/81* | (2006.01) | |
| *A61K 8/86* | (2006.01) | |
| *A61K 8/891* | (2006.01) | |
| *A61Q 5/12* | (2006.01) | |

(52) U.S. Cl.
CPC ............... *A61K 8/062* (2013.01); *A61K 8/31* (2013.01); *A61K 8/416* (2013.01); *A61K 8/8111* (2013.01); *A61K 8/86* (2013.01); *A61K 8/891* (2013.01); *A61Q 5/12* (2013.01); *A61K 2800/48* (2013.01); *A61K 2800/596* (2013.01)

(58) Field of Classification Search
None
See application file for complete search history.

(56) References Cited

U.S. PATENT DOCUMENTS

| | | |
|---|---|---|
| 4,701,432 A | 10/1987 | Welborn, Jr. |
| 5,272,236 A | 12/1993 | Lai et al. |
| 5,322,728 A | 6/1994 | Davey et al. |
| 5,539,021 A | 7/1996 | Pate et al. |
| 6,525,157 B2 | 2/2003 | Cozewith et al. |
| 6,783,766 B2 | 8/2004 | Pate et al. |
| 6,960,635 B2 | 11/2005 | Stevens et al. |
| 2006/0078527 A1* | 4/2006 | Midha ..................... A61Q 5/12 424/70.27 |
| 2015/0374608 A1 | 12/2015 | Gao et al. |

FOREIGN PATENT DOCUMENTS

| | | |
|---|---|---|
| WO | 2014047102 A2 | 3/2014 |
| WO | 2015138210 A1 | 9/2015 |

* cited by examiner

*Primary Examiner* — Jessica Worsham
(74) *Attorney, Agent, or Firm* — Thomas S. Delbert

(57) ABSTRACT

A method of making a hair care composition is provided, comprising: providing a cationic hair care emulsion, comprising: a cationic surfactant; optionally, a nonionic surfactant; water, wherein the water forms a continuous phase; and an internal phase, wherein the internal phase comprises: a cosmetically acceptable hydrocarbon oil; and a polyolefin blend, comprising: a high density polyolefin having a density of $>0.90$ g/cm$^3$; and a low density polyolefin having a density of $\leq 0.90$ g/cm$^3$; wherein the polyolefin blend has an average melt index of $>7$ as measured according to ASTM D 1238; providing a cosmetically acceptable silicone; providing an additional water; providing at least one hair care additive; and combining the cationic hair care emulsion, the cosmetically acceptable silicone, the additional water and the at least one hair care additive to form the hair care composition.

10 Claims, No Drawings

SYNERGISTIC HAIR CARE FORMULATIONS

The present invention relates to a method of making a personal care composition. In particular, the present invention relates to a method of making a hair care composition containing an emulsion of a polyolefin blend.

Personal care products such as leave-on hair conditioners, require a smooth and silky feel to please consumers. Aesthetics are one of the most important factors driving consumer satisfaction with such personal care products. Accordingly, sensory agents, such as silicone oils and silicone elastomer gels have been used to impart favorable aesthetics properties to various personal care products. Nevertheless, these sensory agents have certain associated drawbacks, like insufficient sensory performance, poor conditioning, stability and texture; or have relatively high incorporation costs.

Even where a composition provides desirable performance, it may still be lacking based on how difficult it is to produce the material. For instance, compositions that require high temperature processing or high use amounts of particular additives to achieve the desired performance remain disadvantaged because of the additional costs associated with their production.

A process for facilitating incorporation of certain components into cosmetic formulations is disclosed by Pate et al. in U.S. Pat. No. 6,783,766. Pate et al. disclose a process of preparing an advanced cosmetic product by combining a high internal phase ratio (HIPR) emollient in water emulsion with a partial cosmetic formulation that typically contains water, fragrance, a rheology modifier, or a pH adjuster, or a combination thereof.

Notwithstanding, there remains a continuing need for cost effective manufacturing methods and easily useable agents for use the manufacture of such hair care compositions, wherein the agents provide enhanced frizz control, volume control and sensory properties to the hair care compositions.

The present invention provides a method of making a hair care composition, comprising: providing a cationic hair care emulsion, comprising: 0.1 to 20 wt % of a cationic surfactant; water, wherein the water forms a continuous phase; and 60 to 95 wt % of an internal phase, wherein the internal phase comprises: a cosmetically acceptable hydrocarbon oil; and a polyolefin blend, comprising: a high density polyolefin having a density of >0.90 g/cm$^3$; and a low density polyolefin having a density of ≤0.90 g/cm$^3$; wherein the polyolefin blend has an average melt index of >7 as measured according to ASTM D 1238; providing a cosmetically acceptable silicone; providing an additional water; providing at least one hair care additive; and combining the cationic hair care emulsion, the cosmetically acceptable silicone, the additional water and the at least one hair care additive to form the hair care composition.

The present invention provides a method of making a hair care composition, comprising: providing a cationic hair care emulsion, comprising: 0.1 to 20 wt % of a cationic surfactant; 0 to 20 wt % of a non-ionic surfactant; water, wherein the water forms a continuous phase; and 60 to 95 wt % of an internal phase, wherein the internal phase comprises: a cosmetically acceptable hydrocarbon oil; and a polyolefin blend, comprising: a high density polyolefin having a density of >0.90 g/cm$^3$; and a low density polyolefin having a density of ≤0.90 g/cm$^3$; wherein the polyolefin blend has an average melt index of >7 as measured according to ASTM D 1238; providing a cosmetically acceptable silicone; providing an additional water; providing at least one hair care additive; and combining the cationic hair care emulsion, the cosmetically acceptable silicone, the additional water and the at least one hair care additive to form the hair care composition.

The present invention provides a method of making a hair care composition, comprising: providing a cationic hair care emulsion, comprising: 0.1 to 20 wt % of a cationic surfactant; 0 to 20 wt % of a non-ionic surfactant; water, wherein the water forms a continuous phase; and 60 to 95 wt % of an internal phase, wherein the internal phase comprises: a cosmetically acceptable hydrocarbon oil; and a polyolefin blend, comprising: a high density polyolefin having a density of >0.90 g/cm$^3$; and a low density polyolefin having a density of ≤0.90 g/cm$^3$; wherein the polyolefin blend has an average melt index of >7 as measured according to ASTM D 1238; providing a cosmetically acceptable silicone; providing an additional water; providing at least one hair care additive; and combining the cationic hair care emulsion, the cosmetically acceptable silicone, the additional water and the at least one hair care additive to form the hair care composition; wherein the cationic hair care emulsion provided is substantial free of ethylene-acrylic acid copolymer.

DETAILED DESCRIPTION

We have now found that polyolefin blends as described herein, which are highly effective sensory agents in hair care compositions, may be prepared as cationic hair care emulsions (preferably, a concentrated cationic oil in water emulsions), for instance as high internal phase emulsions where the volume % internal phase is at least 75%. Advantageously, the cationic hair care emulsion is easily incorporated in hair care compositions at low concentrations and eliminates the need for high temperatures to melt the oil gel in the oil phase of such compositions. A hair care composition prepared according to the method of the present invention containing the cationic hair care emulsion (preferably, a concentrated cationic emulsion) provides improved resistance to hair frizziness in high humidity conditions compared to compositions containing oil gel added separately, and compared to commercial silicone-containing benchmarks.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and polyacrylic acid standards. GPC techniques are discussed in detail in Modem Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons.

The term "polymer" as used herein and in the appended claims refers to a compound prepared by polymerizing monomers, whether of the same or a different type. The generic term "polymer" includes the terms "homopolymer," "copolymer," and "terpolymer."

Percentages of monomer units in a polymer are percentages of solids or neat monomer weight, i.e., excluding any water present in a polymer emulsion.

The term "hair care compositions" as used herein and in the appended claims relates to compositions formulated for topical application to hair, in particular, to human hair. Examples of hair care compositions include, but are not limited to, shampoos, leave-on hair conditioners, rinse off hair conditioners, styling gels, hairsprays, and two part hair dyes.

The term "cosmetically acceptable" as used herein and in the appended refers to ingredients typically used in hair care compositions, and is intended to underscore that materials that are toxic when present in the amounts typically found in hair care compositions are not contemplated as part of the present invention.

Preferably, the method of making a hair care composition of the present invention, comprises: providing a cationic hair care emulsion, comprising: 0.1 to 20 wt % (preferably, 0.1 to 10 wt %; more preferably, 0.1 to 6 wt %; most preferably, 0.5 to 4 wt %) of a cationic surfactant (or a mixture of cationic surfactants); 0 to 20 wt % (preferably, 0.1 to 20 wt %; more preferably, 0.1 to 15 wt %; still more preferably, 1 to 10 wt %; most preferably, 3 to 8 wt %) of a nonionic surfactant (or a mixture of nonionic surfactants); 5 to 39.9 wt % (preferably, 10 to 39.9 wt %; more preferably, 10 to 25 wt %) water, wherein the water forms a continuous phase; and 60 to 95 wt % of an internal phase, wherein the internal phase comprises: a cosmetically acceptable hydrocarbon oil; and a polyolefin blend, comprising: a high density polyolefin having a density of >0.90 g/cm$^3$ (as measured according to ASTM D792); and a low density polyolefin having a density of ≤0.90 g/cm$^3$ (preferably, of 0.86 to 0.90 g/cm$^3$) (as measured according to ASTM D792); wherein the polyolefin blend has an average melt index of >7 as measured according to ASTM D 1238; providing a cosmetically acceptable silicone; providing an additional water; providing at least one hair care additive; and combining the cationic hair care emulsion, the cosmetically acceptable silicone, the additional water and the at least one hair care additive to form the hair care composition.

Preferably, the cationic surfactant used in the cationic hair care emulsion provided in the method of the present invention is selected from the group of cosmetically acceptable cationic surfactants. More preferably, the cationic surfactant used in the cationic hair care emulsion provided in the method of the present invention is a quaternary ammonium salt surfactant. Preferably, the quaternary ammonium salt surfactant is selected from the group consisting of dialkyldimethylammonium salt surfactants, alkylbenzyldimethylammonium salt surfactants, alkyltrimethylammonium salt surfactants, alkylpyridinium halide surfactants and mixtures thereof. More preferably, the cationic surfactant used in the cationic hair care emulsion provided in the method of the present invention is a quaternary ammonium salt surfactant selected from the group of quaternary ammonium salt surfactants having a quaternary ammonium cation according to formula (I)

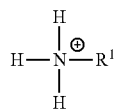

wherein R$^1$ is an alkyl group having an average of 10 to 30 (preferably, 12 to 26; more preferably, 14 to 22; still more preferably, 16 to 20; most preferably, 16) carbons atoms per molecule and mixtures thereof. Preferably, the quaternary ammonium salt surfactants have corresponding anions. Preferably, the corresponding anions are selected from the group consisting of halide ions (e.g., chloride ions), methyl sulfate ions, other anions and mixtures thereof. More preferably, the corresponding anions are halide ions. Preferably, the cationic surfactant used in the cationic hair care emulsion provided in the method of the present invention is selected from the group consisting of behenyltrimethylammonium chloride, cetrimonium chloride and combinations thereof. Most preferably, the cationic surfactant used in the cationic hair care emulsion provided in the method of the present invention is cetrimonium chloride.

Preferably, the cationic hair care emulsion provided in the method of the present invention, comprises: 0.1 to 20 wt % of a cationic surfactant (or a mixture of cationic surfactants). More preferably, the cationic hair care emulsion provided in the method of the present invention, comprises 0.1 to 10 wt % of a cationic surfactant (or a mixture of cationic surfactants). Still more preferably, the cationic hair care emulsion provided in the method of the present invention, comprises 0.1 to 6 wt % of a cationic surfactant (or a mixture of cationic surfactants). Most preferably, the cationic hair care emulsion provided in the method of the present invention, comprises 0.5 to 4 wt % of a cationic surfactant (or a mixture of cationic surfactants).

Preferably, the cationic hair care emulsion provided in the method of the present invention, optionally, further comprises: a nonionic surfactant. Preferably, the nonionic surfactant used in the cationic hair care emulsion provided in the method of the present invention is selected from the group consisting of polyoxyalkylene surfactants, polyalkylene glycol esters, polyoxyethylene derivatives of fatty acid esters of polyhydric alcohols, fatty acid esters of polyalkoxylated polyhydric alcohols, polyalkoxylated natural fats and oils, polyalkylene oxide block copolymers, alkyl polyglucosides, sucrose esters, and mixtures thereof. More preferably, the nonionic surfactant used in the cationic hair care emulsion provided in the method of the present invention is a polyoxyalkylene surfactant. Most preferably, the nonionic surfactant used in the cationic hair care emulsion provided in the method of the present invention is a polyoxyalkylene surfactant, wherein the polyoxyalkylene surfactant is a polyoxyethylene surfactant. Preferably, the polyoxyethylene surfactant is elected from the group consisting of alcohol alkoxylates, alkylphenol alkoxylates and mixtures thereof. Preferred alcohol alkoxylates include, for example, alcohol ethoxylates and alcohol propoxylates. More preferably, the cationic hair care emulsion provided in the method of the present invention, comprises: a nonionic surfactant selected from the group consisting of alcohol ethoxylate that conforms to the formula

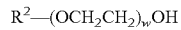

wherein R$^2$ is a C$_{10\text{-}30}$ alkyl group (preferably, a C$_{12\text{-}26}$ alkyl group; more preferably, a C$_{12\text{-}20}$ alkyl group; most preferably, a C$_{12\text{-}18}$ alkyl group); and w has an average value of 10 to 200 (preferably, 10 to 160; more preferably, 12 to 140; most preferably, 20 to 100). Still more preferably, the cationic hair care emulsion provided in the method of the present invention, comprises: a nonionic surfactant selected from the group consisting of a polyethylene glycol ether of lauryl alcohol that conforms to the formula

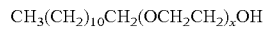

wherein x has an average value of 10 to 30 (preferably, 12 to 26; more preferably, 15 to 25; most preferably, 23); a polyethylene glycol ether of cetyl alcohol that conforms to the formula

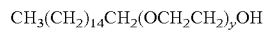

wherein y has an average value of 10 to 30 (preferably, 12 to 26; more preferably, 15 to 25; most preferably, 20); a polyethylene glycol ether of stearyl alcohol that conforms to the formula

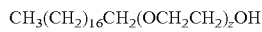

wherein z has an average value of 10 to 160 (preferably, 60 to 140; more preferably, 80 to 120; most preferably, 100); and mixtures thereof. Most preferably, the cationic hair care emulsion provided in the method of the present invention, comprises: a nonionic surfactant selected from the group consisting of laureth-23, ceteth-20, steareth-100 and mixtures thereof.

Preferably, the cationic hair care emulsion provided in the method of the present invention, comprises: 0 to 20 wt % of a nonionic surfactant (or a mixture of nonionic surfactants). More preferably, the cationic hair care emulsion provided in the method of the present invention, comprises 0.1 to 20 wt % of a nonionic surfactant (or a mixture of nonionic surfactants). Still more preferably, the cationic hair care emulsion provided in the method of the present invention, comprises 0.1 to 15 wt % of a nonionic surfactant (or a mixture of nonionic surfactants). Yet more preferably, the cationic hair care emulsion provided in the method of the present invention, comprises 1 to 10 wt % of a nonionic surfactant (or a mixture of nonionic surfactants). Most preferably, the cationic hair care emulsion provided in the method of the present invention, comprises 3 to 8 wt % of a nonionic surfactant (or a mixture of nonionic surfactants).

Preferably, the cationic hair care emulsion provided in the method of the present invention comprises water as a continuous phase. The water generally comprises the balance of the cationic hair care emulsion provided, to bring the cationic hair care emulsion to 100%, after the amounts of the other ingredients have been selected. Preferably, the water constitutes 5 to 39.9 wt % (preferably, 10 to 39.9 wt %; more preferably, 10 to 25 wt %) of the cationic hair care emulsion provided.

Preferably, the cationic hair care emulsion provided in the method of the present invention comprises an internal phase, wherein the internal phase constitutes 60 to 95 wt % of the hair care emulsion. More preferably, the cationic hair care emulsion provided in the method of the present invention contains the internal phase at a high concentration. Preferably, the cationic hair care emulsion of the present invention is a concentrated emulsion. More preferably, the cationic hair care emulsion of the present invention is a high internal phase emulsion (HIPE), wherein the internal phase constitutes ≥75 wt % of the cationic hair care emulsion.

Preferably, the internal phase comprises a first cosmetically acceptable hydrocarbon oil and a polyolefin blend; wherein the polyolefin blend, comprises: a high density polyolefin having a density of >0.90 g/cm$^3$ and a low density polyolefin having a density of ≤0.90 g/cm$^3$ (preferably, of 0.86 to 0.90 g/cm$^3$); wherein the polyolefin blend has an average melt index of >7 as measured according to ASTM D 1238.

Preferably, the average melt index (g/10 min, as measured according to ASTM D 1238) for the high density polyolefin and the low density polyolefin used in the polyolefin blend of the cationic hair care emulsion provided in the method of the present invention is >7. More preferably, the average melt index (g/10 min, as measured according to ASTM D 1238) for the high density polyolefin and the low density polyolefin used in the polyolefin blend of the cationic hair care emulsion provided in the method of the present invention is ≥8. Most preferably, the average melt index (g/10 min, as measured according to ASTM D 1238) for the high density polyolefin and the low density polyolefin used in the polyolefin blend of the cationic hair care emulsion provided in the method of the present invention is ≥8.5.

Preferably, the high density polyolefin used in the polyolefin blend of the cationic hair care emulsion provided in the method of the present invention has a weight average molecular weight of 41,000 to 500,000. More preferably, the high density polyolefin used in the polyolefin blend of the cationic hair care emulsion provided in the method of the present invention has a weight average molecular weight of 70,000 to 90,000. Most preferably, the high density polyolefin used in the polyolefin blend of the cationic hair care emulsion provided in the method of the present invention has a weight average molecular weight of 75,000 to 85,000.

Preferably, the low density polyolefin used in the polyolefin blend of the cationic hair care emulsion provided in the method of the present invention has a weight average molecular weight of 5,000 to 40,000. More preferably, the low density polyolefin used in the polyolefin blend of the cationic hair care emulsion provided in the method of the present invention has a weight average molecular weight of 10,000 to 30,000. Most preferably, the low density polyolefin used in the polyolefin blend of the cationic hair care emulsion provided in the method of the present invention has a weight average molecular weight of 20,000 to 28,000.

Preferably, the high density polyolefin and low density polyolefin used in the cationic hair care emulsion provided in the method of the present invention are produced using a metallocene catalyst. Metallocene catalysis enables control of the polyolefin properties relating to, for example, crystallinity, polymer chain length, and distribution homogeneity of the polymer chain units. Metallocene catalysis also favors uniformity in polymer chains density and length. Suitable metallocene catalysts include, for example, those described in U.S. Pat. Nos. 4,701,432, 5,322,728, and 5,272,236. Preferably, the high density polyolefin and low density polyolefin used in the cationic hair care emulsion provided in the method of the present invention are polyethylenes produced with a metallocene catalyst. Suitable polyethylenes are available from, for example, The Dow Chemical Company under the trademark AFFINITY or ENGAGE (ethylene/octene copolymers), and from Exxon Chemical Company under the trademark EXACT (ethylene/butene copolymers, ethylene/hexene copolymers, or ethylene/butene/hexene terpolymers). Preferably, the polyolefins used in the cationic hair care emulsion provided in the method of the present invention are selected from the group consisting of ethylene/octene copolymers, ethylene/butene copolymers, ethylene/hexene copolymers, ethylene/propylene, ethylene/butene/hexene terpolymers and blends thereof. Preferably, the polyolefins used in the cationic hair care emulsion provided in the method of the present invention include an ethylene octene copolymer. Preferably, the polyolefins used in the cationic hair care emulsion provided in the method of the present invention are propylene/alpha-olefin copolymers. Suitable propylene/alpha-olefin copolymers include, for example, those described in detail in U.S. Pat. Nos. 6,960,635 and 6,525,157. Such propylene/alpha-olefin copolymers are commercially available from The Dow Chemical Company under the trademark VERSIFY, or from ExxonMobil Chemical Company under the trademark VISTAMAXX. Other suitable polyolefins are sold by The Dow Chemical Company under the trademarks AMPLIFY, ATTANE, INFUSE, NORDEL, and VLDPE. Other suitable non-limiting examples of commercially available metallocene catalyzed polyethylenes and the melt index and density of each is as shown in TABLE 1.

TABLE 1

| Polyolefin Name | Melt Index | Density |
|---|---|---|
| AFFINITY GA 1950 | 500 | 0.874 |
| AFFINITY PL1840G | 1 | 0.909 |
| AMPLIFY EA 103 | 21 | 0.930 |
| AMPLIFY GR 202 | 8 | 0.930 |
| ATTANE 4203 | 0.8 | 0.905 |
| ATTANE 4404G | 4 | 0.904 |
| ENGAGE 8100 | 1 | 0.870 |
| ENGAGE 8130 | 13 | 0.863 |
| ENGAGE 8200 | 5 | 0.870 |
| ENGAGE 8402 | 30 | 0.902 |
| INFUSE D9807 | 15 | 0.866 |
| LDPE 4016 | 16 | 0.916 |
| LDPE 640I | 2 | 0.920 |
| LDPE 955I | 35 | 0.923 |
| VERSIFY 2200 | 2 | 0.876 |
| VERSIFY 3200 | 8 | 0.876 |
| VERSIFY 4200 | 25 | 0.876 |

Preferably, the cationic hair care emulsion provided in the method of the present invention is substantially free of ethylene acrylic acid copolymer. Preferably, the cationic hair care emulsion provided in the method of the present invention is substantially free of ethylene acrylic acid (or residues thereof). More preferably, the cationic hair care emulsion provided in the method of the present invention contains <3 wt % of ethylene acrylic acid (or residues thereof). Still more preferably, the cationic hair care emulsion provided in the method of the present invention contains <1 wt % of ethylene acrylic acid (or residues thereof). Yet more preferably, the cationic hair care emulsion provided in the method of the present invention contains <0.1 wt % of ethylene acrylic acid (or residues thereof). Most preferably, the cationic hair care emulsion provided in the method of the present invention contains 0 wt % of ethylene acrylic acid (or residues thereof).

Preferably, the high density polyolefin in the internal phase of the cationic hair care emulsion provided in the method of the present invention constitutes 5 to 30 wt % of solids by weight of the internal phase. More preferably, the high density polyolefin in the internal phase of the cationic hair care emulsion provided in the method of the present invention constitutes 5 to 16 wt % of solids by weight of the internal phase.

Preferably, the low density polyolefin in the internal phase of the cationic hair care emulsion provided in the method of the present invention constitutes 5 to 20 wt % of solids by weight of the internal phase. More preferably, the low density polyolefin in the internal phase of the cationic hair care emulsion provided in the method of the present invention constitutes 5 to 15 wt % of solids by weight of the internal phase.

Preferably, the weight ratio of the high density polyolefin to the low density polyolefin in the polyolefin blend of the cationic hair care emulsion provided in the method of the present invention is 1:95 to 95:1. More preferably, the weight ratio of the high density polyolefin to the low density polyolefin in the polyolefin blend of the cationic hair care emulsion provided in the method of the present invention is 10:40 to 40:10. Still more preferably, the weight ratio of the high density polyolefin to the low density polyolefin in the polyolefin blend of the cationic hair care emulsion provided in the method of the present invention is 1:1 to 3:1. Yet more preferably, the weight ratio of the high density polyolefin to the low density polyolefin in the polyolefin blend of the cationic hair care emulsion provided in the method of the present invention is 1:1 to 2:1. Most preferably, the weigh ratio of the high density polyolefin to low density polyolefin in the polyolefin blend of the cationic hair care emulsion provided in the method of the present invention is selected from the group consisting of 1:1, 1.5:1, 2:1 and 3:1.

Preferably, the cosmetically acceptable hydrocarbon oil used in the cationic hair care emulsion provided in the method of the present invention a cosmetically acceptable hydrocarbon oil. Preferably, the cosmetically acceptable hydrocarbon oil includes a $C_{14-22}$ hydrocarbon oil. More preferably, the cosmetically acceptable hydrocarbon oil is a blend of hydrocarbon oils including at least one $C_{14-22}$ hydrocarbon oil. Most preferably, the cosmetically acceptable hydrocarbon oil is a blend of $C_{14-22}$ hydrocarbon oils. Suitable cosmetically acceptable hydrocarbon oils include, for example, those sold under the trademarks LILAC, GEMSEAL 25, GEMSEAL 40, PERMETHYL 101A, PERMETHYL 99A, SILKFLO 364 NF, SILKFLO 366 NF, FANCOL POLYISO 200-CG, FANCOL POLYISO 300-CG, FANCOL POLYISO 450-CG, FANCOL POLYISO 800-CG, PANALANE L-14E, PURESYN 2, PURESYN 4, or RITA-DECENE 20. A preferred cosmetically acceptable hydrocarbon oil for use in the cationic hair care emulsion provided in the method of the present invention is LILAC white oil.

Preferably, the cosmetically acceptable hydrocarbon oil in the internal phase of the cationic hair care emulsion provided in the method of the present invention constitutes 35 to 95 wt % of the internal phase. More preferably, the first cosmetically acceptable hydrocarbon oil in the internal phase of the cationic hair care emulsion provided in the method of the present invention constitutes 50 to 90 wt % of the internal phase. Most preferably, the first cosmetically acceptable hydrocarbon oil in the internal phase of the cationic hair care emulsion provided in the method of the present invention constitutes 65 to 85 wt % of the internal phase.

Preferably, the internal phase of the cationic hair care emulsion provided in the method of the present invention comprises: 5 to 30 wt % (preferably, 5 to 16 wt %) of the high density polyolefin; 5 to 20 wt % (preferably, 5 to 15 wt %) of the low density polyolefin; and 50 to 90 wt % (preferably, 65 to 85 wt %) of the cosmetically acceptable hydrocarbon oil.

Preferably, the cationic hair care emulsion provided in the method of the present invention optionally further comprises an optional ingredient. Preferably, the optional ingredients include, for example, additional surfactants (e.g., zwitterionic surfactants) and preservatives (e.g., benzoic acid, sorbic acid, phenoxyethanol). More preferably, the cationic hair care emulsion provided in the method of the present invention further comprises a preservative, wherein the preservative is selected from the group consisting of benzoic acid, sorbic acid, phenoxyethanol (preferably, benzoic acid).

Preferably, in the method of making a hair care composition of the present invention, the cationic hair care emulsion provided accounts for 0.1 to 10 wt % (preferably, 0.1 to 5 wt %; more preferably, 0.4 to 2.5 wt %; most preferably, 0.5 to 1.5 wt %) of the hair care composition, by weight of the hair care composition.

The cationic hair care emulsion provided in the method of the present invention can be prepared by a variety of methods, including batch and continuous methods well known in the art. In a preferred continuous method (described generally by Pate et al in U.S. Pat. No. 5,539,021 at column 3, line 15 to column 6, line 27, which is incorporated herein by reference), the cationic hair care emulsion provided in the method of the present invention is prepared by a process wherein a stream containing the continuous phase is flowed through a first conduit and merged continuously with a stream of the internal phase that is flowed through a second conduit. The streams are then merged into a disperser in the presence of the cationic surfactant and the nonionic surfactant, if any. The surfactants can be added to either stream, or as a separate stream. Additional manufacturing details can be found, for instance, in U.S. Pat. No. 6,783,766, which is incorporated herein by reference.

Preferably, the cosmetically acceptable silicone provided in the method of the present invention comprises a cosmetically acceptable silicone selected from the group consisting of amodimethicone, cyclomethicone, dimethicone, dimethiconol, hexadecyl methicone, hexamethyldisiloxane, methicone, phenyl dimethicone, stearoxy dimethicone and mixtures thereof. More preferably, the cosmetically acceptable silicone provided in the method of the present invention comprises a cosmetically acceptable silicone selected from the group consisting of amodimethicone, cyclomethicone, dimethicone, dimethiconol, hexadecyl methicone, methicone and mixtures thereof. Still more preferably, the cosmetically acceptable silicone provided in the method of the present invention comprises a cosmetically acceptable silicone selected from the group consisting of amodimethicone, dimethicone and a mixture thereof. Most preferably, the cosmetically acceptable silicone provided in the method of the present invention is selected from the group consisting of amodimethicone and dimethicone.

Preferably, the cosmetically acceptable silicone provided in the method of the present invention, accounts for 0.1 to 10 wt % of the hair care composition, by weight of the hair care composition. More preferably, the cosmetically acceptable silicone provided in the method of the present invention, accounts for 0.1 to 5 wt % (more preferably, 0.4 to 2.5 wt %; most preferably, 0.5 to 1.5 wt %) of the hair care composition, by weight of the hair care composition.

Preferably, the at least one hair care additive provided in the method of the present invention, includes at least one hair care additive selected from the group consisting of an additional surfactant; a thickener; a humectant, an excipient and mixtures thereof. Preferably, the at least one hair care additive provided in the method of present invention, includes an additional surfactant, at least one thickener, at least one humectant and at least one excipient. More preferably, the at least one hair care additive provided in the method of present invention, includes an additional surfactant, at least one thickener, at least one humectant and at least one excipient; wherein the hair care composition is selected from the group consisting of a leave on hair conditioner and a rinse off hair care conditioner.

Preferably, the additional surfactants are selected from the group consisting of anionic surfactants (as described herein above with respect to the cationic hair care emulsion), cationic surfactants (as described herein above with respect to the cationic hair care emulsion), zwitterionic surfactants, nonionic surfactants (as described herein above with respect to the cationic hair care emulsion) and mixtures thereof. More preferably, the additional surfactants are selected from the group consisting of cationic surfactants, nonionic surfactants and anionic surfactants and mixtures thereof. Most preferably, the additional surfactants are selected from the group consisting of cationic surfactants, nonionic surfactants and mixtures thereof.

Preferably, the thickeners are selected to increase the viscosity of the hair care composition, preferably without substantially modifying the other properties of the hair care composition. Preferably, the thickeners are selected from the group consisting of polysaccharides (e.g., xanthan gum, guar gum, starch, and vegetable gum) and cellulosic polymers (e.g., carboxymethyl cellulose (CMC), hydroxymethyl cellulose (HMC), and hydroxypropyl methyl cellulose (HPMC)). Certain preferred thickeners include, for example, hydrophobically modified cross-linked acrylate copolymers (e.g., those sold by Lubrizol under the trademark CARBOPOL ULTREZ 21).

Preferably, the at least one hair care additive provided in the method of the present invention, includes a thickener. More preferably, in the method of making a hair care composition of the present invention, the at least one hair care additive provided includes a thickener, wherein the thickener accounts for 0 to 1.0 wt % (preferably, 0.1 to 1.0 wt %; more preferably, 0.2 to 0.7 wt %; most preferably, 0.3 to 0.5 wt %) of the hair care composition, by weight of the hair care composition.

Preferably, the humectants are selected to inhibit the loss of moisture. Preferably, the humectants are selected from the group consisting of glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, polymeric polyols, and mixtures thereof.

Preferably, the at least one hair care additive provided in the method of the present invention, includes a humectant. More preferably, in the method of making a hair care composition of the present invention, the at least one hair care additive provided includes a humectant, wherein the humectant accounts for 0 to 20.0 wt % (preferably, 1 to 20.0 wt %; more preferably, 2 to 15 wt %; most preferably, 5 to 10 wt %) of the hair care composition, by weight of the hair care composition.

Preferably, the excipients are selected from the group consisting of additional emollients (e.g., hydrocarbon oils, esters, natural oils), waxes, sensory modifiers, lubricants, preservatives (e.g., benzoic acid, sorbic acid, phenoxyethanol), antioxidants (e.g., butylated hydroxytoluene), chelating agents, antimicrobials, pH adjusting agents/buffers/neutralizing agents, sunscreen actives, vitamins, proteins/amino acids, plant extracts, natural ingredients, bio-actives, fragrances/perfumes, penetrants, polymers/resins/hair fixatives/film formers, surfactants/detergents/emulsifiers/opacifying agents, volatiles/propellants/solvents/carriers, liquid vehicles/solvents/carriers, salts, anti-static agents, anti-frizz agents, antidandruff agents, hair waving/straightening agents, absorbents, colorants, hard particles, and conditioning agents.

Preferably, in the method of making a hair care composition of the present invention, additional water is provided in excess of the water provided with the cationic hair care emulsion. The additional water provided generally comprises the balance of the hair care composition, to bring the hair care composition to 100 wt %, after the amounts of the other required and optional ingredients have been selected.

Preferably, in the method of making a hair care composition of the present invention, the additional water provided accounts for 1 to 98.0 wt % (preferably, 25 to 98 wt %; more preferably, 50 to 95 wt %; most preferably, 60 to 92 wt %) of the hair care composition, by weight of the hair care composition.

Preferably, the method of making a hair care composition of the present invention, comprises: providing a cationic hair care emulsion according to the present invention; providing a cosmetically acceptable silicone; providing an additional water; providing at least one hair care additive; and combining the cationic hair care emulsion, the cosmetically acceptable silicone, the additional water and the at least one hair care additive to form the hair care composition. More preferably, the method of making a hair care composition of the present invention, comprises: providing a cationic hair care emulsion according to the present invention; providing a cosmetically acceptable silicone; providing an additional water; providing at least one hair care additive; and combining the cationic hair care emulsion, the cosmetically acceptable silicone, the additional water and the at least one hair care additive to form the hair care composition; wherein the hair care composition is selected from the group consisting of a shampoo, a leave-on hair conditioner, a rinse off hair conditioner, a styling gel, a hairspray and a two part hair dye. Most preferably, the method of making a hair care composition of the present invention, comprises providing a cationic hair care emulsion according to the present invention; providing a cosmetically acceptable silicone; providing an additional water; providing at least one hair care additive, wherein the at least one hair care additive includes an excipient and a thickener; and combining the cationic hair care emulsion, the cosmetically acceptable silicone, the additional water and the at least one hair care additive to form the hair care composition; wherein the hair care composition is selected from the group consisting of a leave on hair conditioner and a rinse off hair care conditioner.

Preferably, in the method of making a hair care composition of the present invention, the cosmetically acceptable silicone and the at least one hair care additive can be added to a dispersion of the cationic hair care emulsion in the additional water. Preferably, in the method of making a hair care composition of the present invention, the cationic hair care emulsion can be added to an aqueous mixture of the additional water, the cosmetically acceptable silicone and the at least one hair care additive.

Some embodiments of the present invention will now be described in detail in the following Examples.

Synthesis P1: Polyolefin Gel

A polyolefin gel was synthesized in an oil jacketed five gallon batch mixer (Model #VME-12 available from Fryma Maschinen AG, Switzerland) equipped with a sweep mixing blade. The mixer was loaded with 4,788 g of isohexadecane (Permethyl 101A from Presperse) and the sweep mixing blade was turned on at a speed of 60 rpm. A blend of Affinity™ PL1840G (456 g, available from The Dow Chemical Company) and Affinity™ GA1950 (456 g, available from The Dow Chemical Company) was then slowly added to the batch mixer. The contents of the batch mixer were then heated to 117° C. with agitation. Once at temperature, the contents of the batch mixer were allowed to continue mixing for an additional 60 minutes. The set point temperature was then reduced to 66° C. After an additional 150 minutes of mixing the temperature of the contents of the batch mixer had dropped below 70° C. The product polyolefin gel was recovered from the batch mixer and stored for later use.

Synthesis E1: Cationic Polyolefin Gel Emulsion

An internal phase of a cationic polyolefin gel emulsion was prepared by forming a combination having 3 wt % steareth-100, 3 wt % laureth-23, 0.75 wt % benzoic acid and 93.25 wt % of a polyolefin gel prepared according to Synthesis P1 and heating the combination to 100° C. The combination was then mixed for an additional 1 minute with a propeller mixer to form an internal phase material. The internal phase material was then loaded into a Nordson Altablue 4TT hot melter (with the reservoir and delivery line temperature controls both been set to 110° C.) and pumped at a rate of 14 g/min into a two inch diameter rotor stator mixer heated to 110° C. and spinning at 850 rpm where it was merged with a deionized water stream flowing at 1.0 ml/min and an aqueous stream of 30% active cetrimonium chloride flowing at 0.5 ml/min to form a cationic polyolefin gel emulsion. The cationic polyolefin gel emulsion formed had a volume mean particle size of 2.7 microns and was flowed into a second two inch diameter rotor stator mixer heated to 110° C. and spinning at 450 rpm where it was combined with a deionized water stream flowing at 2 ml/min to dilute the cationic polyolefin gel emulsion down to 80 vol % internal phase. The cationic polyolefin gel emulsion was then passed through an exit tubing set to 90° C. and having a backpressure regulator set to 50 psi and collected.

Synthesis E2: Nonionic Concentrated Emulsion

An internal phase of a nonionic concentrated emulsion was prepared by forming a combination having 3 wt % ceteth-20, 3 wt % laureth-23, 0.75 wt % benzoic acid and 93.25 wt % of the polyolefin gel prepared according to Synthesis P1 and heating the combination to 100° C. The combination was then mixed for 1 minute with a propeller mixer to form an internal phase material. The internal phase material was then loaded into a Nordson Altablue 4TT hot melter (with the reservoir and delivery line temperature controls both been set to 110° C.) and pumped at a rate of 20 g/min into a two inch diameter rotor stator mixer heated to 110° C. and spinning at 850 rpm where it was merged with a deionized water stream flowing at 1.75 ml/min to form a nonionic polyolefin gel emulsion. The nonionic polyolefin gel emulsion formed had a volume mean particle size of 1.3 microns and was flowed into a second two inch diameter rotor stator mixer heated to 110° C. and spinning at 450 rpm where it was combined with a deionized water stream flowing at 2.5 ml/min to dilute the nonionic polyolefin gel emulsion down to 82.5 vol % internal phase. The nonionic polyolefin gel emulsion was then passed through an exit tubing set to 90° C. and having a backpressure regulator set to 50 psi and collected.

Synthesis E3: Anionic Concentrated Emulsion

An internal phase of an anionic concentrated emulsion was prepared using a polyolefin gel prepared according to Synthesis P1 as the internal phase. The internal phase was heated to 100° C. until it became clear and uniform. The internal phase was then loaded into a Nordson Altablue 4TT hot melter (with the reservoir and delivery line temperature controls both been set to 110° C.) and pumped at a rate of 14 g/min into a two inch diameter rotor stator mixer heated to 110° C. and spinning at 900 rpm where it was merged with a deionized water stream flowing at 0.8 ml/min and a stream of Empicol® ESB70 (70 wt % sodium laureth sulfate in water) flowing at 0.7 ml/min to form an anionic polyolefin gel emulsion. The anionic polyolefin gel emulsion formed had a volume mean particle size of 0.5 microns and was flowed into a second two inch diameter rotor stator mixer heated to 110° C. and spinning at 450 rpm where it was combined with a deionized water stream flowing at 3 ml/min to dilute the anionic polyolefin gel emulsion down to 78 vol % internal phase. The anionic polyolefin gel emulsion was then passed through an exit tubing set to 90° C. and having a backpressure regulator set to 50 psi and collected.

Synthesis E4: Cationic Concentrated Emulsion

An internal phase of a cationic polyolefin gel emulsion was prepared by forming a combination having 6 wt % behentrimonium chloride, 0.75 wt % benzoic acid and 93.25 wt % of a polyolefin gel prepared according to Synthesis P1 and heating the combination to 110° C. The combination was then mixed for an additional 1 minute with a propeller mixer to form an internal phase material. The internal phase material was then loaded into a Nordson Altablue 4TT hot melter (with the reservoir and delivery line temperature controls both been set to 110° C.) and pumped at a rate of 15.3 g/min into a two inch diameter rotor stator mixer heated to 110° C. and spinning at 850 rpm where it was merged with a deionized water stream flowing at 1.5 ml/min. The cationic polyolefin gel emulsion formed had a volume mean particle size of 1.8 microns and was flowed into a second two inch diameter rotor stator mixer heated to 110° C. and spinning at 450 rpm where it was combined with a deionized water stream flowing at 2.5 ml/min to dilute the cationic polyolefin gel emulsion down to 79.3 vol % internal phase. The cationic polyolefin gel emulsion was then passed through an exit tubing set to 90° C. and having a backpressure regulator set to 50 psi and collected.

Synthesis E5: Cationic Concentrated Emulsion

An internal phase of a cationic polyolefin gel emulsion was prepared by forming a combination having 6 wt % stearamidopropyl dimethylamine, 0.75 wt % benzoic acid and 93.25 wt % of a polyolefin gel prepared according to Synthesis P1 and heating the combination to 110° C. The combination was then mixed for an additional 1 minute with a propeller mixer to form an internal phase material. The internal phase material was then loaded into a Nordson Altablue 4TT hot melter (with the reservoir and delivery line temperature controls both been set to 110° C.) and pumped at a rate of 16.5 g/min into a two inch diameter rotor stator mixer heated to 110° C. and spinning at 850 rpm where it was merged with a deionized water stream flowing at 1.25 ml/min. The cationic polyolefin gel emulsion formed had a volume mean particle size of 0.87 microns and was flowed into a second two inch diameter rotor stator mixer heated to 110° C. and spinning at 450 rpm where it was combined with a deionized water stream flowing at 2.5 ml/min to dilute the cationic polyolefin gel emulsion down to 81.5 vol % internal phase. The cationic polyolefin gel emulsion was then passed through an exit tubing set to 90° C. and having a backpressure regulator set to 50 psi and collected.

Synthesis B1: Conditioner Base

Deionized water (89.85 g) was added to a flask outfitted with a heating mantle and a stirring bar. The water was then heated to 80-90° C. In a beaker, cetearyl alcohol (6.0 g), cetrimonium chloride (0.2 g), ceteareth 20 (0.3 g), glycerin (1.0 g), propylene glycol (0.5 g, PG USP), and butylated hydroxytoluene (0.05 g) were combined and heated to 80 to 90° C. When up to temperature and the oil phase was melted, the beaker contents were then poured into the flask with stirring at 800 rpm. The resulting flask contents were then stirred for an hour while maintaining the temperature set point for the flask contents at 80 to 90° C. The heating mantle was then removed and the flask contents were allowed to cool with continued stirring. When the flask contents reached 45° C., Kathon™ CG preservative (0.1 g)(available from The Dow Chemical Company) was added to the flask contents with continued stirring. When the flask contents reached room temperature a PPG-14 butyl ether copolymer (1.0 g)(UCON™ Fluid AP available from The Dow Chemical Company) was added to the flask contents with continued stirring to provide a conditioner base formulation.

Comparative Examples C1-C13 and Example 1-6

Rinse off hair care conditioner formulations were prepared in each of Comparative Examples C1-C13 and Examples 1-6 using the following procedure. First, the initial water was added to a flask in the amount noted in TABLE 2. The water was then heated at a set point temperature of 80° C. with continuous stirring at 300 rpm. Then, disodium ethylenediaminetetraacetic acid (0.1 g, Na$_2$EDTA), cetearyl alcohol (5.5 g), stearamidopropyl dimethylamine (1.5 g), lactic acid (0.52 g), butylated hydroxytoluene (0.05 g, BHT) and mineral oil (if any, in the amount noted in TABLE 2 added as a second cosmetically acceptable hydrocarbon oil) were added to the flask in the order listed while maintaining the set point temperature at 80° C. with continuous stirring at 300 rpm. The stir rate was then increased to 400 rpm and behenrimonium chloride (0.3 g) was added to the contents of the flask while maintaining the temperature set point at 80° C. with continuous stirring. Once the behenrimonium chloride was observed to completely melt into the contents of the flask, the heating source was then removed. Once the contents of the flask cooled to 65° C., the additional water was added to the flask in the amount noted in TABLE 2 with continuous stirring. Once the contents of the flask cooled to 60° C., the cationic concentrated emulsion (if any, in the amount noted in TABLE 2) prepared according to Example E1, E4 or E5 was added to the flask with continuous stirring. Once the contents of the flask cooled to 35° C., Kathon™ CG preservative (0.1 g)(available from The Dow Chemical Company) was added with continuous stirring to provide the resulting rinse off hair conditioner formulation.

TABLE 2

| Ex. # | Initial Water (g) | Mineral Oil[1] (g) | Dimethicone (g) | Amodimethicone (g) | Additional water (g) | Product Synthesis Ex # | (g) |
|---|---|---|---|---|---|---|---|
| C1 | 55.20 | — | — | — | 36.73 | — | — |
| C2 | 54.60 | 1.0 | — | — | 36.33 | — | — |
| C3 | 54.60 | — | — | 1.0 | 36.33 | — | — |
| C4 | 54.56 | — | — | — | 36.37 | E1 | 1.0 |
| C5 | 53.96 | — | — | — | 35.97 | E1 | 2.0 |
| C6 | 54.60 | 0.5 | — | — | 36.33 | E1 | 0.5 |

TABLE 2-continued

| Ex. # | Initial Water (g) | Mineral Oil[1] (g) | Dimethicone (g) | Amodimethicone (g) | Additional water (g) | Product Synthesis Ex # | (g) |
|---|---|---|---|---|---|---|---|
| C7 | 54.6 | 0.5 | 0.5 | — | 36.33 | — | — |
| C8 | 54.6 | 0.5 | — | 0.5 | 36.33 | — | — |
| C9 | 54.6 | — | 0.5 | 0.5 | 36.33 | — | — |
| C10 | 54.60 | — | — | — | 36.37 | E4 | 1.0 |
| C11 | 54.6 | 0.5 | — | — | 36.33 | E4 | 0.5 |
| C12 | 54.6 | — | — | — | 36.37 | E5 | 1 |
| C13 | 54.6 | 0.5 | — | — | 36.33 | E5 | 0.5 |
| 1 | 54.60 | — | 0.5 | — | 36.33 | E1 | 0.5 |
| 2 | 54.60 | — | — | 0.5 | 36.33 | E1 | 0.5 |
| 3 | 54.6 | — | 0.5 | — | 36.33 | E4 | 0.5 |
| 4 | 54.6 | — | — | 0.5 | 36.33 | E4 | 0.5 |
| 5 | 54.6 | — | 0.5 | — | 36.33 | E5 | 0.5 |
| 6 | 54.6 | — | — | 0.5 | 36.33 | E5 | 0.5 |

[1]LILAC™ $C_{14-22}$ alkane blend available from Sonoborn LLC.

Comparative Example C14

A rinse off hair care conditioner formulation was prepared in Comparative Example C14 using the following procedure. First, initial water (54.60 g) was added to a flask. The water was then heated at a set point temperature of 80° C. with continuous stirring at 300 rpm. Then, disodium ethylenediaminetetraacetic acid (0.1 g, $Na_2EDTA$), cetearyl alcohol (5.5 g), stearamidopropyl dimethylamine (1.5 g), lactic acid (0.50 g), butylated hydroxytoluene (0.1 g, BHT) and dimethicone (1.0 g) were added to the flask in the order listed while maintaining the set point temperature at 80° C. with continuous stirring at 300 rpm. The stir rate was then increased to 400 rpm and behenrimonium chloride (0.3 g) was added to the contents of the flask while maintaining the temperature set point at 80° C. with continuous stirring. Once the behenrimonium chloride was observed to completely melt into the contents of the flask, the heating source was then removed. Once the contents of the flask cooled to 65° C., additional water (36.3 g) was added to the flask with continuous stirring. Once the contents of the flask cooled to 35° C., Kathon™ CG preservative (0.1 g)(available from The Dow Chemical Company) was added with continuous stirring to provide the resulting rinse off hair conditioner formulation.

Rinse Off Hair Conditioner Formulation Testing

Rinse off hair conditioner formulations prepared according to Comparative Examples C4-C6 and C14 and Examples 1-2 were each performance tested on separate 5 g hair samples (Brazilian Curly Hair w/ 20 cm of length, International Hair Importers, Inc.). The hair samples were first washed with 0.5 g of shampoo (SEDA Cachos Definidos shampoo available from Unilever Products in Brazil). Then the hair samples were rinsed with water for 30 seconds. Finally, rinse off hair care conditioner formulations (0.5 g) were added to separate hair samples and massaged in for 30 seconds. Then the hair samples were again rinsed with water for 30 seconds. The water used for rinsing in this testing was softened to a hardness of 80 ppm and heated to 38° C. The hair samples were then dried for 24 hours at ambient temperature (about 22° C.). The dried hair samples were then sensory evaluated by 6 people who classified the hair samples from best (10) to worst (1) for each of hair definition, frizz control, volume control and sensory. The average results of the panel evaluations are provided in TABLE 3.

TABLE 3

| Ex. # | Definition | Frizz Control | Volume Control | Sensory | Total Sensorial |
|---|---|---|---|---|---|
| Shampoo | 9.0 | 7.8 | 6.4 | 6 | 29.2 |
| C1 | 5.8 | 3.4 | 3.8 | 3.2 | 16.2 |
| C2 | 5.6 | 3.2 | 2.0 | 5.2 | 16.0 |
| C3 | 3.8 | 5.2 | 7.6 | 4.6 | 21.2 |
| C4 | 4.6 | 6.4 | 6.2 | 8.6 | 25.8 |
| C5 | 5.4 | 5.2 | 4.8 | 6.6 | 22.0 |
| C6 | 6.4 | 7.6 | 6.6 | 6.4 | 27.0 |
| C14 | 1 | 1.6 | 1.4 | 2.8 | 6.8 |
| 1 | 5.8 | 5.4 | 7.2 | 4.8 | 23.2 |
| 2 | 7.4 | 9.2 | 9.0 | 6.8 | 32.4 |

Rinse Off Hair Conditioner Formulation Testing

Rinse off hair conditioner formulations prepared according to Comparative Examples C1-C3, C7-C11 and C14 and Examples 3-4 were each performance tested on separate 5 g hair samples (Brazilian Curly Hair w/ 20 cm of length, International Hair Importers, Inc.). The hair samples were first washed with 0.5 g of shampoo (SEDA Cachos Definidos shampoo available from Unilever Products in Brazil). Then the hair samples were rinsed with water for 30 seconds. Finally, rinse off hair care conditioner formulations (0.5 g) were added to separate hair samples and massaged in for 30 seconds. Then the hair samples were again rinsed with water for 30 seconds. The water used for rinsing in this testing was softened to a hardness of 80 ppm and heated to 38° C. The hair samples were then dried for 24 hours at ambient temperature (about 22° C.). The dried hair samples were then sensory evaluated by 6 people who classified the hair samples from best (13) to worst (1) for each of hair definition, frizz control, volume control and sensory. The average results of the panel evaluations are provided in TABLE 4.

TABLE 4

| Ex. # | Definition | Frizz Control | Volume Control | Sensory | Total Sensorial |
|---|---|---|---|---|---|
| Shampoo | 8.3 | 8.6 | 7.4 | 9.2 | 33.5 |
| Shampoo + cond.[1] | 10.9 | 8.6 | 10.8 | 8.8 | 39.1 |
| C1 | 2.0 | 4.7 | 1.9 | 2.3 | 10.9 |
| C2 | 2.2 | 5.0 | 2.7 | 1.5 | 11.4 |
| C3 | 8.5 | 6.0 | 9.1 | 8.0 | 31.6 |

TABLE 4-continued

| Ex. # | Definition | Frizz Control | Volume Control | Sensory | Total Sensorial |
|---|---|---|---|---|---|
| C7 | 7.8 | 9.6 | 10.6 | 8.8 | 36.8 |
| C8 | 10.4 | 4.5 | 10.2 | 11.5 | 36.6 |
| C9 | 9.1 | 5.4 | 8.3 | 10.9 | 33.7 |
| C10 | 9.1 | 5.4 | 9.9 | 6.7 | 31.1 |
| C11 | 3.1 | 6.2 | 1.5 | 3.3 | 14.1 |
| C14 | 7.1 | 11.1 | 6.9 | 5.6 | 30.7 |
| 3 | 8.4 | 9.4 | 8.1 | 10.6 | 36.5 |
| 4 | 4.1 | 6.6 | 4.1 | 1.5 | 16.3 |

[1]SEDA Cachos Definidos conditioner available from Unilever Products in Brazil.

Rinse Off Hair Conditioner Formulation Testing

Rinse off hair conditioner formulations prepared according to Comparative Examples C1-C3, C7-C9 and C12-14 and Examples 5-6 were each performance tested on separate 5 g hair samples (Brazilian Curly Hair w/ 20 cm of length, International Hair Importers, Inc.). The hair samples were first washed with 0.5 g of shampoo (SEDA Cachos Definidos shampoo available from Unilever Products in Brazil). Then the hair samples were rinsed with water for 30 seconds. Finally, rinse off hair care conditioner formulations (0.5 g) were added to separate hair samples and massaged in for 30 seconds. Then the hair samples were again rinsed with water for 30 seconds. The water used for rinsing in this testing was softened to a hardness of 80 ppm and heated to 38° C. The hair samples were then dried for 24 hours at ambient temperature (about 22° C.). The dried hair samples were then sensory evaluated by 6 people who classified the hair samples from best (13) to worst (1) for each of hair definition, frizz control, volume control and sensory. The average results of the panel evaluations are provided in TABLE 5.

TABLE 5

| Ex. # | Definition | Frizz Control | Volume Control | Sensory | Total Sensorial |
|---|---|---|---|---|---|
| Shampoo | 8.1 | 7.2 | 6.3 | 4.8 | 26.4 |
| Shampoo + cond.[1] | 12.4 | 12.5 | 12.8 | 12.9 | 50.6 |
| C1 | 11.3 | 12 | 11.1 | 11.2 | 45.6 |
| C2 | 5.1 | 6.6 | 4.2 | 5.0 | 20.9 |
| C3 | 6.7 | 7.5 | 8.0 | 7.3 | 29.5 |
| C7 | 3.9 | 3.0 | 4.9 | 3.5 | 15.3 |
| C8 | 4.9 | 3.5 | 7.1 | 7.4 | 22.9 |
| C9 | 2.1 | 2.8 | 2.6 | 5.1 | 12.6 |
| C12 | 9.4 | 8.7 | 9.4 | 10.3 | 37.8 |
| C13 | 12.1 | 11.5 | 11.4 | 10.4 | 45.4 |
| C14 | 1.4 | 2.1 | 1.0 | 3.7 | 8.2 |
| 5 | 7.8 | 7.0 | 7.1 | 5.8 | 27.7 |
| 6 | 5.8 | 6.6 | 4.8 | 6.2 | 23.4 |

[1]SEDA Cachos Definidos conditioner available from Unilever Products in Brazil.

We claim:

1. A method of making a hair care composition, comprising:
    providing a cationic hair care emulsion, comprising:
        0.1 to 20 wt % of a cationic surfactant, wherein the cationic surfactant is selected from the group consisting of quaternary ammonium cations according to formula (I)

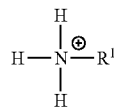

wherein $R^1$ is an alkyl group having an average of 10 to 30 carbons atoms per molecule;
        0.1 to 20 wt % of a nonionic surfactant selected from the group consisting of a polyoxyalkylene surfactant;
        5 to 39.9 wt % water, wherein the water forms a continuous phase; and
        60 to 95 wt % of an internal phase, wherein the internal phase comprises:
            50 to 90 wt %, based on weight of the internal phase, of a cosmetically acceptable hydrocarbon oil, wherein the cosmetically acceptable hydrocarbon oil is a blend of $C_{14-22}$ hydrocarbon oils; and
            a polyolefin blend, comprising:
                5 to 30 wt %, based on weight of the internal phase, of a high density polyolefin having a density of >0.90 g/cm$^3$ and a weight average molecular weight of 70,000 to 90,000 Daltons; and
                5 to 20 wt %, based on weight of the internal phase, of a low density polyolefin having a density of ≤0.90 g/cm$^3$ and a weight average molecular weight of 10,000 to 30,000 Daltons;
            wherein the polyolefin blend has an average melt index of >7 as measured according to ASTM D 1238;
    providing a cosmetically acceptable silicone, wherein the cosmetically acceptable silicone is selected from the group consisting of amodimethicone, dimethicone and a mixture thereof;
    providing an additional water;
    providing at least one hair care additive; and
    combining the cationic hair care emulsion, the cosmetically acceptable silicone, the additional water and the at least one hair care additive to form the hair care composition; wherein the hair care composition comprises: 0.1 to 10 wt % of the cationic hair care emulsion, 0.1 to 10 wt % of the cosmetically acceptable silicone; and 1 to 98 wt % of the additional water.

2. The method of claim 1, wherein the cationic hair care emulsion provided, contains 3 to 8 wt % of the nonionic surfactant, based on weight of the cationic hair care emulsion; wherein the nonionic surfactant is selected from the group consisting of laureth-23, ceteth-20, steareth-100 and mixtures thereof.

3. The method of claim 2, wherein the cationic hair care emulsion provided contains <0.1 wt % of ethylene-acrylic acid or residues thereof.

4. The method of making a hair care composition of claim 1, wherein the at least one hair care additive provided includes an excipient.

5. The method of making a hair care composition of claim 4, wherein the at least one hair care additive provided further includes a thickener.

6. The method of claim 5, wherein the hair care composition is selected from the group consisting of a leave on hair conditioner and a rinse off hair care conditioner.

7. The method of claim 1, wherein the at least one hair care additive provided includes an additional surfactant, a thickener, a humectant and an excipient; and wherein the hair care composition is selected from the group consisting of a leave on hair conditioner and a rinse off hair care conditioner.

8. The method of claim 7, wherein the at least one hair care additive includes a thickener; and wherein the thickener accounts for 0.1 to 1 wt % of the hair care composition, by weight of the hair care composition.

9. The method of claim 7, wherein the at least one hair care additive includes a humectant; and wherein the humectant accounts for 1 to 20 wt % of the hair care composition, by weight of the hair care composition.

10. The method of claim 1, wherein the polyoxyalkylene surfactant is selected from the group consisting of alcohol ethoxylate surfactants that conform to the formula $$R^2-(OCH_2CH_2)_w OH$$

wherein $R^2$ is a $C_{10-30}$ alkyl group; and w has an average value of 10 to 200.

\* \* \* \* \*